United States Patent [19]
Law et al.

[11] Patent Number: 5,130,141
[45] Date of Patent: Jul. 14, 1992

[54] COMPOSITIONS FOR AND METHODS OF TREATING MUSCLE DEGENERATION AND WEAKNESS

[76] Inventors: Peter K. Law, 2277 Union Ave. A702, Memphis, Tenn. 38104; Tena G. Goodwin, 4134 Coventry Dr., Memphis, Tenn. 38127

[21] Appl. No.: 708,801

[22] Filed: May 30, 1991

Related U.S. Application Data

[63] Continuation of Ser. No. 529,209, May 25, 1990, abandoned, which is a continuation of Ser. No. 198,038, May 24, 1988, abandoned.

[51] Int. Cl.$^5$ .......................... A61K 35/34; C12N 5/00
[52] U.S. Cl. .................................... 424/548; 514/907; 514/11
[58] Field of Search ................... 514/907, 11; 424/548

[56] References Cited

PUBLICATIONS

Law et al VI International Congress on Neuromuscular Diseases, vol. 9, No. 55/Supplement Abstract 46.14, 1986.
Partridge et al J. of NIH Research, Jul./Aug. 1989, vol. 1 Research Briefs.
M. G. Wang and P. K. Law, *Proceeding of the International Union of Physiological Sciences*, 16:14 (1986).
H. J. Li et al., *Abstracts, Society of Neuroscience*, 12:1289 (1986).
P. K. Law., *Neuroscience, The Second World Congress of Neuroscience*, Abst., 22:5595.
Law and Goodwin, *IV International Congress on Neuromuscular Diseases* Abst. 9, (1986).
Stephen D. Hauschka et al., *Pathogenesis of Human Muscular Dystrophies*, Amsterdam, Excerpa Medica, pp. 835-855, (1977).
Peterson A. C. and Pena S., *Muscle and Nerve*, 7:194-203.
Law, *Exp. Neurol.*, 60:231, (1978).
Law, et al., *Muscle and Nerve*, 2:356, (1979).
Law, *Muscle and Nerve*, 5:619, (1982).
Watt et al., *Muscle and Nerve*, 742-749, Nov./Dec. 2984.
Law and Goodwin, *Fifth Biennial Forum Regeneration Abst.*, p. 18, (1985).
Law and Goodwin, *Soc. Neurosi Abst.*, 11:1302 (1985).

*Primary Examiner*—Howard E. Schain
*Assistant Examiner*—Choon P. Koh

[57] ABSTRACT

Compositions for and methods of treating muscle weakness and degeneration are described. Such compositions include myogenic cells which are administered by the described methods to one or more affected muscles.

22 Claims, 2 Drawing Sheets

COMPOSITIONS FOR AND METHODS OF TREATING MUSCLE DEGENERATION AND WEAKNESS

This is a continuation of application Ser. No. 529,209, filed May 25, 1990, which is a continuation of application Ser. No. 198,038, filed May 24, 1988, now abandoned.

The invention described herein was made in the course of or under grants from the National Institute of Health.

BACKGROUND OF THE INVENTION

This invention pretains to compositions for and methods of treating muscle degeneration and weakness. More particularly, the present invention relates to myogenic cells and methods of using such cells in the treatment of muscle degeneration and weakness.

Progressive degeneration and weakness of skeletal muscles are hallmarks of the forty human neuromuscular diseases affecting motoneurones, peripheral nerves and/or muscles. Most of these diseases are fatal, and all are crippling. There is no known cure or effective treatment. These diseases include motoneurone disorders, such as Amyotrophic Lateral Sclerosis (ALS) and neuromuscular junction disorders, such as Myasthenia Gravis and Eaton-Lambert Syndrome. Also included are the twelve hereditary muscular dystrophies, predominantly muscle diseases, affecting over 200,000 Americans. In the muscular dystrophies, dystrophic cells degenerate because of the lack of normal genome.

Muscular dystrophy in the mouse is characterized by progressive degeneration of skeletal muscles in the hindlimbs and in the chest wall. Dystrophic symptoms first appear at 20 to 30 days after birth and consist of sporadic flexion and flaccid extension of the hindlimbs. Occasionally, the dystrophic mouse walks with duck feet (See for example, Michelson et al., *Proc. Nat. Acad. Sci.*, 41: 10798, (1955) and Meier et al., *Life Sci.*, 9: 137, (1970)). A number of approaches have been employed by researchers in the field to study and develop methods to treat the muscular dystrophies and other neuromuscular disorders.

In the case of the hereditary neuromuscular disorders, one approach to correct the genetic disease is to correct the abnormal gene itself. However, before gene therapy can be used to treat hereditary myopathies, the defective genes and their expression have to be determined. Although identification of the dystrophic genes and their primary protein abnormalities has been attempted by some workers, thus far, attempts at identification have not been completely successful. (See e.g., Monaco et al., *Nature* 323: 646-650, 1986; Brown et al., *Hum. Genet.* 71: 62-74, 1985). Furthermore, before gene therapy can be used to treat hereditary myopathies, the problems of nonspecific gene integration, replacement, targeting, regulation and expression also have to be overcome. The high spontaneous mutation rate also complicates the process of identification and prevention. (See e.g., Epstein et al., *Am Sci* 65: 703-711, 1977.) When normal and dystrophic tissues are compared, the dystrophy-specific protein difference is often masked by the concomitant presence of individual-specific protein differences (see, e.g., Komi et al., *Acta. Physiol. Scand.* 100:385-392, 1977) and secondary degenerative changes (See, e.g., Dolan et al., *Exp. Neurol.* 47:105-117, 1975). In situations where the primary protein abnormality is not known, any trial of drugs to treat the disease will necessarily be arbitrary and its success coincidentally limited. (See, e.g., Bhargava et al., *Exp. Neurol.* 55:583-602, 1977.)

In Duchenne muscular dystrophy, carrier detection and prenatal diagnosis seek prevention rather than cure. See, e.g., Bechmann, *Isr. J. Med Sci* 13:102-106, 1977. These are inadequate measures, because not all sex-linked carriers—inasmuch as they are phenotypically normal—are exposed to the diagnostic tests. There are also the legal, religious, emotional and financial considerations involved in inducing an abortion.

Various studies have been carried out in attempts to develop methods to treat neuromuscular disease.

In one reported approach, mouse muscle mince transplants studies were conducted on normal and dystrophic littermates (Law, *Exp. Neurol.*, 60:231, 1978). In another study, it is reported that near-normal contractile properties were produced in adult dystrophic mouse muscle by grafting a muscle of a newborn normal mouse into a recipient muscle of a dystrophic mouse (Law et al., *Muscle & Nerve*, 2:356, 1979). It is also been reported that mesenchyme transplantation can improve the structure and function of dystrophic mouse muscle as demonstrated by histological, electrophysiological and mechanophysiological studies (Law, *Muscle & Nerve*, 5:619, 1982).

Watt et al., *Muscle and Nerve*, 741-749, Nov/Dec, 1984, report the injection of normal myoblasts into apparently abnormal muscle of strain mdx mice, but do not report any improvement in muscle function, The mdx mice do not exhibit any muscle weakness. Myoabnormality of central nucleation heals itself with age.

It has further been reported that injections of normal myoblasts into growing dystrophic mouse solei improved the structure and function of the solei (Law and Goodwin, *Fifth Biennial Forum Regeneration Abst*, 1985, page 18; Law and Goodwin, *Soc. Neurosi. Abst.* 11:212, 1985; and Law and Goodwin, IV International Congress on Neuromuscular diseases, Abst. 9, 1986). Improved muscle function was determined only by electrophysiological and mechanophysiological studies. In such studies, only one muscle, the soleus, rather than all major muscle groups were tested. The soleus, containing many red fibers that are slow twitching, is unique and different from other muscles in the body that are composed of fast twitching fibers.

Various attemps have been made to provide treatments for neuromuscular disorders. However, none have achieved recovery of muscle function, locomotive pattern and respiratory function in a host affected with muscle degeneraion and weakness. Thus, compositions and methods of treating such disorders are being sought.

SUMMARY OF THE INVENTION

The present invention provides, for the first time, compositions for and methods of successfully treating muscle degeneration and weakness. The present invention also teaches the use of cloned cells for the successful in vivo treatment of such disorders.

Accordly, the present invention provides a method of treating muscle degeneration and weakness in a host which comprises administering a treatment effective amount of myogenic cells to at least one myopathic muscle of the host.

Although any myogenic cell may be used in the practice of the present invention, preferred cells include myoblasts, myotube cells and young muscle fiber cells. These myogenic cells may be cultured or cloned. They may further be histocompatible or histoincompatible with the recipient.

Thus, the present invention provides compositions for and methods of treating muscle degeneration and weakness which are expected to enhance the function and quality of life of hosts who suffer such disorders.

Phase contrast. Bar=50 um.

Figure 2A:
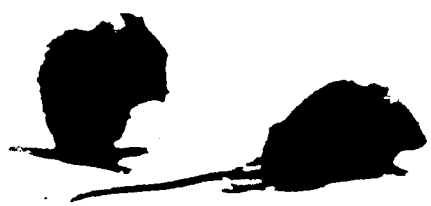

FIG. 2A shows the dystrophic mouse, responding favorably to myoblast injection and CsA-treatment, standing on its hindlimbs.

Figure 2B:
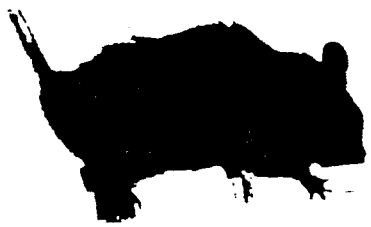

FIG. 2B shows the dystrophic mouse, responding favorably to myoblast injection and CsA-treatment, grasping the glass rod with toes of the hindlimbs.

Figure 2C:

FIG. 2C shows the dystrophic mouse, responding favorably to myoblast injection and CsA treatment, balancing itself on a glass rod.

Figure 3:
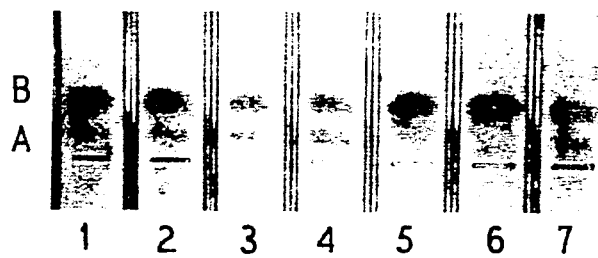

FIG. 3 shows the result of agarose gel electrophoresis of muscle GPI-1AA (slow-migrating band) in Lane 1- CsA treated, normal extensors; Lane 2- CsA-treated, normal flexors; Lane 3 - CsA-treated, dystrophic extensors; Lane 4- CsA-treated, dystrophic flexors. The presence of GPI-1AA indicates survival of donor myoblasts two months postoperatively. GPI-1AA was absent in Lane 5- normal extensors, without CsA-treatment; Lane 6- Dystrophic flexors, without CsA-treatment; Lane 7- control GPI-1AA, GPI-1BB.

Figure 4:

FIG. 4 shows the rear legs of a CsA-treated dystrophic mouse two months after it received myoblast injections in the right leg. The contralateral leg was left intact.

Figure 5A:

FIG. 5A shows a micrograph of a cross section of normal tibialis anterior muscle without CsA-treatment after myoblast injection.

Figure 5B:

FIG. 5B shows micrograph of a cross-section of dystrophic tibialis anterior muscle without CsA-treatment after myoblast injection.

Figure 5C:

FIG. 5C shows a micrograph of a cross-section of a normal tibialis anterior muscle from a CsA-treated mouse having immature (donor) cells at arrow.

Figure 5D:
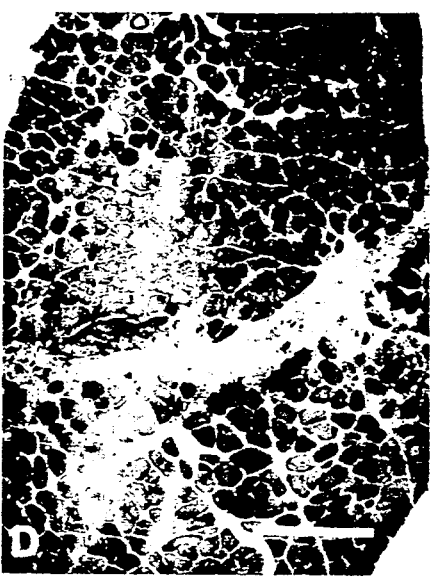

FIG. 5D shows a micrograph of a cross-section of dystrophic tibialis anterior muscle from a CsA-treated mouse having immature (donor) cells as shown at the arrow.

With respect to FIG. 5 all cross-sections are all of the same magnification. Modified Gomori trichrome stain. Bar=400 um.

DETAILED DESCRIPTION OF THE INVENTION

The present invention provides, for the first time, compositions for and methods of successfully treating disorders such as muscle degeneration and weakness, for example, that accompanying neuromuscular disease. It was unexpectedly found that the claimed compositions and methods may be used to dramatically improve the muscle function, locomotive pattern and respiratory function of a host suffereing such disorders. Such treatment has not heretofore been achieved. It is also believed that the present invention demonstrates the first use of clonal cells for the successful in vivo treatment of such disorders.

The claimed compositons and methods will be illustrated for the treatment of mice having hereditary muscular dystrophy. However, other mammals and other neuromuscular diseases and muscle degeneration and weakness and may be treated by the inventive compositions and methods.

Dystrophic cells degenerate because of the lack of the normal genome, and it has surprisingly been found that the claimed compositions and methods may be used to incorporate the normal genome into dystrophic muscle to dramatically improve the function of the muscle.

Two mechanisms are thought to be responsible for the incorporation of the normal genome in such cases:

1. Surviving donor myoblasts develop into normal myofibers and replace the degenerative tissue; and
2. Normal myoblasts fuse with dystrophic cells to form genetically mosiac myofibers of normal phenotype.

Because the claimed compositions and methods are based on developmental processes universal to all mammals, it is expected to have broad clinical applications and to minimize problems relating to specificity of integration, complementation, regulation, and expresson of the normal genome inserted should be minimized.

In the treatment of hereditary neuromuscular diseases by use of the claimed invention, it is not necessary to know which gene(s) is responsible for the disease. Furthermore, the administration of genetically normal myogenic cells directly into the dystrophic muscle eliminates the uncertainty of tissue targeting encountered with gene therapy.

It is believed that any myogenic cell may be used in the practice of the present invention. However, preferred myogenic cells include myoblasts, myotube cells and young muscle fiber cells. Such myogenic cells may be either cultured or cloned. The myogenic cells may further be histocompatible or histoincompatible with the recipient.

Myogenic cells may be cultured by a variety of methods known to those skilled in the art to produce a sufficient quantity of cells for use in the claimed invention. One such method is described by Law and Goodwin, *Muscle and Nerve,* 1988, In Press.

Myogenic cells for use in the present invention may also be produced by cloning methods known to those skilled in the art. Whereas both cultured and cloned myogenic cells can provide a virtually unlimited supply of cells, cloned myogenic cells offer advantages over cultured myogenic cells in that cells having superior developmental characteristics may be selected and propagated for the practice of the present invention. Another advantage is that cloned myogenic cells, e.g., myoblasts, can be readily prepared which are essentially free from other cell types. In contrast, cultured myoblasts derived from mesenchyme comprise about 80% myoblasts and 20% fibroblasts and may contain other cell types and components. In some instances, it has been found that fibroblasts interfere with the practice of the claimed invention and cause detrimental effects. (See, Law and Goodwin, 1988, supra.) The use of clonal cell transplants to treat muscle degeneration and weakness and neuromuscular diseases has not been reported. Furthermore, cell clones are physiologically different from organs that are used in heart, lung, kidney and liver transplants.

In order to reduce immunological rejection problems, myogenic cells may be cultured or cloned from muscle biopsies of normal parents or siblings of the dystrophic patients to minimize immunologic reaction (Hauschka et al., In Rowland LP (ed): *Pathogenesis of Human Muscular Dystrophies Ex. Med.*, p. 835, Amsterdam, (1977)). If a host is diagnosed as having a hereditary neuromuscular disease at an early enough age, i.e., when cells are very young and regular, cell biopsies of such cells may be taken and maintained for later culturing or cloning for use in accordance with the present invention. Cloning further removes the more active antigenic factors such as leukocytes, (Lafferty et al., *Transplant Proc.*, 8:349, (1976) and Lafferty et al., *Ann. Rev. Immunol.*, 1:143, (1983)) and can be used to mass-produce the myoblasts (Feder et al., *Sci. Amer.*, 248:36 (1983)).

Although it is desirable to use histrocompatable cells in the practice of the present invention, it has been found that it is not necessary. Histoincompatible cloned cells were unexpectedly found to dramatically improve muscle function in living hosts.

In accordance with the present invention, the myogenic cells are injected into one or more of the muscles of the host with a neuromuscular disorder, or in the case of a host with a hereditary neuromuscular disease, into a presumably pre-myopathic muscle. As used herein, "presumptively myopathic" means that a host has tested positive for a hereditary neuromuscular disease but does not demonstrate any apparent symptoms or pathology of the disease. The number and type of muscles selected for administration of the compositions of the claimed invention will depend upon the severity of the condition being treated and will ultimately be decided by the attending physician or veterinarian.

The present invention teaches that administration of an immunosuppressant to a host allows histoincompatible clones of normal myogenic cells administered to the host to survive and develop in the skeletal muscles, thereby greatly improving muscle structure and function, and preventing or reducing muscle weakness, a primary cause of crippling and respiratory failure in hereditary muscular dystrophies. The immunosuppressant cyclosporin-A (CsA, Sandoz) was used, enabling clones of histoincompatible normal myoblasts to survive, develop, and to improve the structure and function of the dystrophic host muscles. However, other immunosupressants which are or may become known to those skilled in the art will find application in the present invention.

The demonstration that CsA administration permits cloned normal myoblasts to survive and develop in histoincompatible hosts indicates that clonal cell lines of superior myoblasts can be established, selected against tumorigenicity, and stored in cell "banks" ready for injection.

The dystrophic mouse is used as an animal model of hereditary muscle degeneration and weakening. Dystrophic mice and control normal mice were treated with the immunosuppressant CsA prior to adminstration of cloned myoblast cells to various muscles as described below in the Examples. Injection of histocompatible normal myoblast clones into dystrophic muscles improved the structure and function of the muscles to almost normal. Immunosuppression of the C57BJ/6J—$dy^{2J}/dy^{2J}$ hosts was by way of daily subcutaneous injection of CsA.

Injected dystrophic muscles exhibited greater cross-sectional area, total fiber number, wet weight, and twitch and tetanus tensions six months postoperatively. Fiber typing was more defined and they contained more normal-appearing and less abnormal-appearing fibers than non-injected controls.

Eleven out of nineteen mice that received myoblasts injections on both sides of the body showed such behavioral improvement that their locomotive patterns were indistinguishable from normal mice. Using dimeric isozymes as genotype markers for host and donor cells, the demonstration of parental and hybrid isozymes inside the injected muscles substantiated the survival and development of donor myoblasts into normal myofibers, and the fusion of normal myoblasts with dystrophic satellite cells to form genetically mosaic myofibers.

The amount of CsA necessary to accomplish effective immunosuppression may be determined by methods known to those skilled in the art. Successful usage of CsA on mice has been reported with subcutaneous injection daily at 50 mg/kg body weight with a stock solution of 15 mg/ml, (Kunki et al., *J. Immunol.*, 125:2526, 1980; and Klaus, et al., *Transplantation*, 31:266, 1981 through the use of doubling, (Watt et al., *Clinl. Exp. Immunol.*, 55:419, 1984 and Watt et al., *Transplantation*, 31:255, 1981) or halfing (Gulati et al., *Exp. Neurol.*, 77: 378, (1982)) of the dosage has also been reported.

Figure 1A:
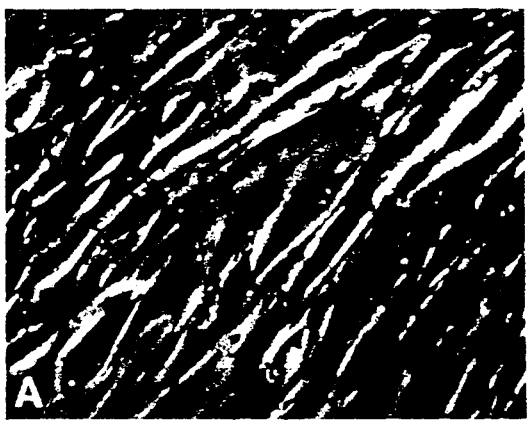
FIG. 1A shows a micrograph of G8 myoblasts used for injection.
Figure 1C:
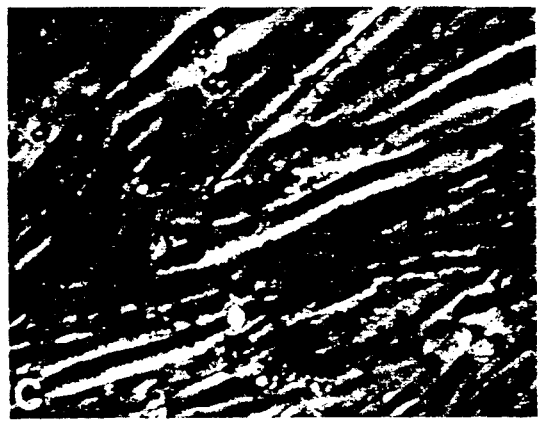
FIG. 1C shows a micrograph of myotube formation 50 hours after plating in the presence of CsA at 25 ug/ml.
Figure 1B:
FIG. 1B shows a micrograph of the formation of myotubes 50 hours after plating.
Figure 1D:
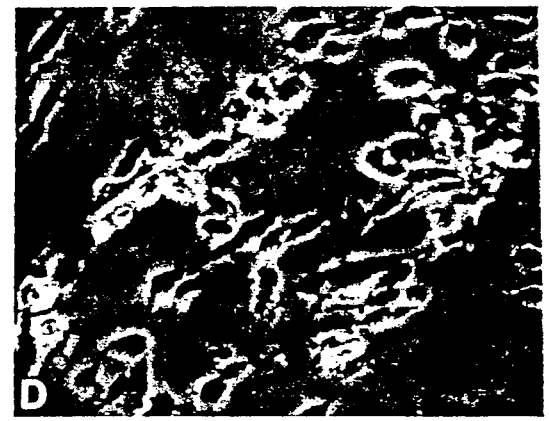
FIG. 1D shows a micrograph of degenerative myoblasts 50 hours after plating in the presence of CsA at 75 ug/ml.

Before carrying out the work described above, a study was conducted to determine CsA toxicity on clonal myoblasts of the mouse. The myoblasts were cultured at CsA concentration of 0, 0.25, 7.50, 25, 75, 250, 562.5 or 750 ug/ml culture medium. It was found that myoblasts survived and fused at CsA concentrations of 25 ug/ml or lower and that they degenerated at 75 ug/ml or higher. Results of this study are illustrated in FIG. 1. FIG. 1A shows G8 myoblasts subcultures that had undergone over twenty serial passages, and were originated from Swiss Webster mose hindlimb muscles, (Christian et al., infra.) FIG. 1B shows myotube formation at 50 hours after plating and FIG. 1C shows myotube formation of 50 hours in the presence of CsA. FIG. 1D shows degenerative myoblasts 50 hours after plating in the presence of CsA at 75 ug/ml. In FIG. 1: Phase Contrast; Bar=50 um.

Cloned myogenic cells may be administered as taught by the present invention for research purposes or may be administered therapeutically to mammals, including humans.

The methods of the claimed invention can be used to administer myogenic cells ("the active ingredient") for the in vivo treatment of mammalian species by physicians and/or veterinarians. The amount of said active ingredient will, of course, depend upon the severity of the condition being treated, the route of administration chosen and the activity or potency of the active ingredient, and ultimately will be decided by the attending physician or veterinarian. Such amount of active ingredient as determined by the attending physician or veterinarian is also referred to herein as a "treatment effective" amount.

The active ingredient may be administered by any route appropriate to the disorder being treated. Although the compositions of the present invention are preferably injected into one or more muscles of the mammal being treated, other acceptable methods, e.g., surgical implantation, will become apparent to those skilled in the art. It is readily appreciated that the preferred route may vary with the disorder being treated.

While it is possible for the active ingredient to be administered as the pure or substantially pure cells, it is preferable to present it as a pharmaceutical formulation or preparation.

The formulations to be used in the practice of the present invention, both for veterinary and for human use, comprise myogenic cells, as described above, together with one or more pharmaceutically acceptable carriers therefor and optionally, other therapeutic ingredients. The carriers must be "acceptable" in the sense of being compatible with the other ingredients of the formulation and not deleterious to the recipient thereof. Such carriers are well known to those skilled in the art of pharmacology. Desirably, the formulation should not include other substances with which myogenic cells are known to be incompatible. In accordance with acceptable pharmacological standards. All methods include the step of bringing into association the active ingredient with a carrier which may constitute one or more accessory ingredients.

Formulations suitable for administration by injection conveniently comprise sterile aqueous solutions of the myogenic cells, which solutions are preferably isotonic with the blood of the recipient. Such formulations may be conveniently prepared by following Good Laboratory Practice to produce a pharmacologically acceptable sterile aqueous solution.

The claimed invention will be further understood with reference to the following examples which are purely exemplary in nature and are not meant to be utilized to limit the scope of the invention.

EXAMPLES

1. Animals

Heterozygous breeders of the hosts were designated C57BL/6J-+/$dy^{2J}$ gpi-1b/1b (Bar Harbor Laboratories, Bar Harbor, ME). Host mice could be phenotypically normal (+/+, +/$dy^{2J}$), or dystrophic ($dy^{2J}$/$dy^{2J}$), with murine dystrophy being inherited in an autosomal recessive pattern. These mice produced glucosephosphate isomerase GP1-1BB (mol. Wt. 134,000 daltons), which was used as a genotype marker to identify the host cells. Mice of either sex and aged 20 days were used as hosts. At this age, dystrophic symptoms began to appear.

2. Immunosuppression

In this study, host mice were primed (Rucker et al., *Transplantation*, 34: 356, (1982)) one week with CsA injected subcutaneously everyday at 50 mg/kg body weight before receiving myoblasts. The same CsA treatment continued until the sacrifice of the host mice. Since the CsA stock solution has a concentration (15 mg/ml) higher than the tolerable level for G8 myoblast (25 ug/ml), CsA was injected in small volume (from about 70 to about 100 ul) on the back of the mice away from the donor cells.

3. Donor Myoblasts

G8-1 Cell Line. It is reported by Christian et al., *Science* 196:995 (1977) that: "The clonal line, G-8, was subcultured from M114, an uncloned myogenic cell line which arose spontaneously in a culture of cells dissociated from Swiss Webster mouse hindlimb muscle. Subculture took place after the M114 cells underwent approximately six generations. The G-8 cells were subcultured 15 time (an estimated 50 cell divisions) without loss of the ability to form myotubes. Multinucleated spherical cells also are found in some older cultures. Well-differentiated G-8 myotubes possess striations and closely resembled normal mouse myotubes in morphology. Many G-8 myotubes contract spontaneously. Clonal myotubes were similiar to cultured mouse embryomyotubes with respect to acetylcholine sensitivity and other membrane resistance characteristics. They differ primarily in the resting membrane potential and in the variation in sensitivity to acetylcholine at different sites on the membrane surface. This may indicate that normal myotubes mature more quickly in vitro than do clonal myotubes. The clonal myotubes can form synapses with neurogenic cells."

The G8-1 myoblasts used in the examples, below, are subclones from the G8 cell line. They can be purchased from The American Type Culture Collection (ATCC) at a serial passage of about fourteen. These cells retain the above capabilities as studied in our laboratories. Cell doubling time is about 22.5 hours. When seeded at optimal concentration ($2 \times 10^6$ in 25 ml of culture medium in a 72 cm² Falcon flask), the myoblasts will undergo mitosis for about 48 hours and then start to fuse.

Maintenance of G8-1 myoblasts. The cell culture prodedure used to culture the G8 myoblasts is modified from that of Christian et al. supra. The cells, purchased in lots of $10^6$ from ATCC, are incubated at 36° C. in 10% $CO_2$ in G8-1 medium consisting of 95% Dulbecco's MEM with 5% fetal bovine serum, penicillin (50 units/ml), sodium salt, and streptomycin sulfate (50 ug/ml) in 72 cm² Falcon plastic flasks, with collagen. The culture medium is changed overnight to remove the dimethyl-sulfoxide and dead cell debris. Initial cell concentration was $2 \times 10^6$ in 25 ml per 72 cm² flask. They are further cultured in fresh medium for 48 hours. When cultures become 60% confluent and just before cell fusion occurs, the myoblasts are dissociated with 5 ml of 0.02% crude trypsin in Hank's balance salt solution ($Ca^{2+}$ and $Mg^{2+}$- free). Cell dissociation is hastened with occasional shaking and gentle scraping with a rubber policeman. Generally, dissociation is completed in 5 minutes. The action of trypsin is stopped immediately by adding an equal amount of horse serum or fetal calf serum. Myoblasts are settled with mild centrifugation and the serum which is antigenic, is replaced by Dulbecco's MEM. A cell count is made on a haemocytometer after the cells are distributed homogenously in the solution by gentle shaking. The cells are then centrifuged at 180 g for 7 minutes. The supernatant is discarded and the cells are ready for transplant.

For regular maintenance, half of the cells are frozen and stored in 10% dimethyl-sulfoxide in mouse medium at each "split". About $10^6$ cells per ml are frozen first in the freezer and then in the Revco deep freezer (−90°). 1 ml of cells are stored in 2 ml vials. The remaining half of the cells are used to maintain the culture. They are sub-cultured in mouse medium at 20-fold lower cell concentration and incubated in 10% $CO_2$. Cell fusion is avoided by subculturing before 60% confluence and by not feeding the fusion medium (2% fetal bovine serum, 98% Dulbecco's MEM). Yaffe (Research In Muscle Development and the Muscle Spindle, Banker, B. et al. p. 110–112, *Excepta Medica*: N.Y. 1972.) indicates that rat cells grown in nutritional medium supplemented with 20% fetal bovine serum and 10% embryo extract proliferate but do not fuse until they become very crowded (REF).

4. Myoblast Transplant

Nine dystrophic (C57BL/6J-dy $^{2J}$/dy$^{2J}$) mice and twelve normal littermates received normal myoblasts injections into their hindlimb and intercostal muscles. Donor myoblasts were clones of G8 cell line (ATCC) originally derived from limb muscles of the Swiss Webster mice (Christian et al., *Science*, 196: 995, (1977)).

Injection was conducted in a sterile laminar flow hood in a microsurgery room equipped with U-V lights. Aseptic precautions were taken. Host mice were awake without anesthesia and were restrained during injection. About $8 \times 10^6$ donor myoblasts were loaded with mild suction into a tuberculin syringe via a 30 gauge needle that was sterile. About $10^6$ myoblasts were injected into each of the following muscle groups on both sides of the host: the quadriceps, femoris, hamstrings, adductors, extensors, flexors, peroneal and the external intercoastal muscles. The needle was slowly withdrawn as the myoblasts were injected. The unavoidable minor damages to fine nerve branches, capillaries, and muscle fibers would trigger axonal sprouting, capillary reformation and muscle regeneration. The wound sealed by itself as the needle was retracted, leaving the muscles "filled" with the pre-determined quantity of myoblasts.

5. Monitor of Behavior and Locomotion

Two to four months later, eleven of the dystrophic mice showed such behavioral improvement that their locomotive patterns were indistinguishable from those of the unoperated normal mice. This improvement is illustrated by use of the photographs in FIG. 2. Sporadic flexion and flaccid extension of their hindlimbs were not seen (FIG. 2A). They were able to use their hindlimbs and toes (FIG. 2B). Their hindlimb muscles were strong enough to support them and to allow them to balance themselves on a glass rod (FIG. 2C). Occasionally they would still walk on duck feet. The mouse could now run. Muscle bulk was increased in both legs and in the chest. Two other mice showed intermediate improvement indicating that there were some functional recovery of the muscles. However, when they were tested on the glass rod their hindlimbs were not strong enough to hold on to the glass rod. Sporadic flexion and flaccid extension of the hindlimbs could still be demonstrated. The remaining eight dystrophic mice did not show significant behavioral improvement. Normal littermates treated similarly were hyperactive, showed enlarged leg and intercoastal muscles, but were otherwise normal.

Whereas the untreated dystrophic mouse dies at about eight months after birth, four dystrophic mice treated in accordance with the claimed invention, have survived over ten months with significant muscle improvement.

6. Monitor of Muscle Genotypes

The survival of G8 clonal myoblasts in muscles of CsA-treated or non-treated C57BL/6J normal or dystrophic mice was also examined two months post-operatively. Host and donor cells exhibited different genotype markers, i.e., muscle isoenzeymes of glucosephosphate isomerase (GPI). Donor G8 myoblasts produced GPI-1AA and host cells produced GPI-1BB. All of the injected muscles of the CsA-treated normal mice showed GPI-1AA, indicating the survival of donor myoblasts in these host muscles. Similarly, all of the injected muscles of the CsA-treated dystrophic mice showed GPI-1AA (FIG. 3). GPI-1AB was also observed in five test muscles, indicating that donor myoblasts fused with host satellite cells. (Data not shown in FIG. 3.) GPI-1AA was not present in the myoblast-injected muscles of the normal or the dystrophic mice without CsA treatment (FIG. 3). Only GPI-1BB representing the host cells was observed in the agarose gell electrophoresis. Donor myoblasts did not survive without immunosuppressant. (b) The survival and development of donor cells in the host muscles were also demonstrated in another series of experiments in which only the right legs received myoblast injections, with the left legs serving as controls. The injected leg showed muscle enlargement (FIG. 4) which was not observable in the contralateral leg. Such muscle enlargement was present in the CsA-treated hosts but not in those without CsA-treatment, regardless of whether the host was normal or dystrophic. These results were obtained from twelve mice from each of the four groups two months after myoblast injection.

7. Monitor of Muscle Phenotypes

FIG. 5 shows cross-sections of the tibialis anterior muscle of both normal and dystophic mice with varing CsA treatment. Histologically, there was no indication of the presence of donor cells in the myoblast-injected normal muscles without CsA treatment (FIG. 5A). These muscle preparations, showing polyclonal myofibers with peripheral nuclei and minimal intercellular connective tissue, were as normal as any intact normal controls. Similarly, the dystrophic muscles receiving myoblast injections but no CsA treatment (FIG. 5B) did not differ from the intact dystrophic controls. However, both CsA-treated normal (FIG. 5C) and dystrophic (FIG. 5D) muscles showed immature and developing myogenic cells that were not observed in non-treated preparations and were thus likely to be donor in origin. Two months was not long enough for all of the donor cells to mature, (See for example, B. M. Carlson: In Mauro A (ed): *Muscle Regeneration*, Raven press, p. 57, (1979) and Carlson et al., In Muro (ed): *Muscle Regeneration*, p. 493, Raven Press, New York, (1979)). Nonetheless, there was a significant improvement in muscle structure in eleven of the CsA-treated dystrophic mice (FIG. 5D) as compared to the non-treated dystrophic ones (FIG. 5B), both receiving normal myoblasts. Dystrophic characteristics such as muscle fiber splitting, central nucleation, phagocytic necrosis, variation in fiber shape and size, and increase in intercellular connective tissues were rarely present in the CsA-treated dystrophic muscle receiving normal myoblasts.

The invention has been described in detail, including the preferred embodiments thereof. However, it will be appreciated that those skilled in the art may make modifications and improvements upon consideration of the specification and drawings as described herein.

What is claimed is:

1. A method of treating muscle degeneration and weakness in a host, comprising the steps of:
    culturing genetically normal myogenic cells from donors to produce a supply of the myogenic cells comprising myoblasts, myotubes, and young muscle fiber cells;
    administering a therapeutically effective dosage of an immunosuppressant to the host; and
    thereafter selecting and administering from the said supply a therapeutically effective dosage of myogenic cells to at least one myopathic muscle of the host,
whereby muscle functions, locomotive patterns, and respiratory functions are improved.

2. The method of claim 1, wherein said selected, therapeutically effective dosage of the cultured myogenic cells is approximately $10^6$ per ml.

3. The method of claim 1, wherein said cultured myogenic cells are obtained from donors selected from a genetically normal group, comprising the parents of the host, siblings of the host, and the host prior to the onset of the muscle degeneration and weakness.

4. The method of claim 1, wherein said immunosuppressant comprises cyclosporin-A.

5. The method of claim 1, wherein said cultured myogenic cells are histocompatible with the host.

6. The method of claim 1, wherein said cultured myogenic cells are histoincompatible with the host.

7. A method of treating muscle degeneration and weakness in a host, comprising the steps of:
cloning genetically normal myogenic cells from donors,
maintaining the cloned myogenic cells in a culture medium to produce a supply of the cloned myogenic cells comprising myoblasts, myotubes, and young muscle fiber cells;
administering a therapeutically effective dosage of an immunosuppressant; and
thereafter selecting and administering from the said supply a therapeutically effective dosage of myogenic cells to at least one myopathic muscle of a host, whereby muscle functions, locomotive patterns, and respiratory functions are improved.

8. The method of claim 7, wherein said myogenic cells are cloned from muscle belonging to donors selected from a genetically normal group, comprising parents and siblings of the host and the host prior to the onset of the muscle degeneration and weakness.

9. The method of claim 7, wherein said selected, therapeutically effective dosage of the cloned myogenic cells is approximately $10^6$ per ml.

10. The method of claim 7, wherein said immunosuppressant comprises cyclosporin-A.

11. The method of claim 7, wherein said cloned myogenic cells are histocompatible with the host.

12. The method of claim 7, wherein said cloned myogenic cells are histoincompatible with the host.

13. A composition for the treatment of muscle degeneration and weakness of a host, comprising:
a supply quantum of cultured genetically normal myogenic cells from donors comprising myoblasts, myotubes, and young muscle fiber cells; and
a therapeutically effective dosage of the myogenic cells from said supply for administration to at least one myopathic muscle of a host.

14. The composition defined in claim 13, wherein said selected therapeutically effective dosage of the cultured myogenic cells is approximately $10^6$ per ml.

15. The composition defined in claim 13, wherein said cultured myogenic cells are obtained from donors selected from a genetically normal group, comprising the parents of the host, siblings of the host, and the host prior to the onset of the muscle degeneration and weakness.

16. The composition defined in claim 13, wherein said cultured myogenic cells are histocompatible with the host.

17. The composition defined in claim 13, wherein said cultured myogenic cells are histoincompatible with the host.

18. A composition for the treatment of muscle degeneration and weakness of a host, comprising:
a supply quantum of cloned genetically normal myogenic cells from donors comprising myoblasts, myotubes, and young muscle fiber cells; and
a therapeutically effective dosage of the myogenic cells selected from said supply for administration to at least one myopathic muscle of a host.

19. The composition defined in claim 18, wherein said selected therapeutically effective dosage of the cloned myogenic cells is approximately $10^6$ per ml.

20. The composition defined in claim 18, wherein said cloned myogenic cells are obtained from donors selected from a genetically normal group, comprising the parents of the host, siblings of the host, and the host prior to the onset of the muscle degeneration and weakness.

21. The composition defined in claim 18, wherein said cloned myogenic cells are histocompatible with the host.

22. The composition defined in claim 18, wherein said cloned myogenic cells are histoincompatible with the host.

* * * * *